United States Patent
Wismann (10) Patent No.: US 10,595,968 B2
(45) Date of Patent: Mar. 24, 2020

(54) TOOTH IMPLANT

(71) Applicant: Horst Wismann, Kelowna (CA)

(72) Inventor: Horst Wismann, Kelowna (CA)

(*) Notice: Subject to any disclaimer, the term of this patent is extended or adjusted under 35 U.S.C. 154(b) by 0 days.

(21) Appl. No.: 15/021,545

(22) PCT Filed: Oct. 3, 2014

(86) PCT No.: PCT/CA2014/050956
§ 371 (c)(1),
(2) Date: Mar. 11, 2016

(87) PCT Pub. No.: WO2015/051453
PCT Pub. Date: Apr. 16, 2015

(65) Prior Publication Data
US 2016/0228218 A1    Aug. 11, 2016

Related U.S. Application Data (60) Provisional application No. 61/888,455, filed on Oct. 8, 2013.

(51) Int. Cl.
*A61C 8/00* (2006.01)

(52) U.S. Cl.
CPC ............ *A61C 8/0062* (2013.01); *A61C 8/006* (2013.01); *A61C 8/0022* (2013.01); *A61C 8/0036* (2013.01); *A61C 8/0037* (2013.01); *A61C 8/0054* (2013.01); *A61C 8/0057* (2013.01); *A61C 8/0059* (2013.01); *A61C 8/0065* (2013.01); *A61C 8/0066* (2013.01); *A61C 8/0086* (2013.01)

(58) Field of Classification Search
CPC ... A61C 8/0062; A61C 8/0022; A61C 8/0036; A61C 8/0037; A61C 8/0054; A61C 8/0057; A61C 8/0059; A61C 8/006; A61C 8/0065; A61C 8/0066; A61C 8/0086
USPC ............ 433/172–176, 201.1, 201.01, 53, 74; 285/120.1, 137, 239
See application file for complete search history.

(56) References Cited

U.S. PATENT DOCUMENTS

| | | | |
|---|---|---|---|
| 3,618,212 A | | 11/1971 | Weissman |
| 4,731,085 A | * | 3/1988 | Koch ................... A61C 8/0018 433/173 |
| 5,052,931 A | * | 10/1991 | Kirsch ................ A61C 8/0018 433/173 |
| 5,092,771 A | | 3/1992 | Tatum |
| 5,197,881 A | * | 3/1993 | Chalifoux ............ A61C 8/0018 433/173 |

(Continued)

FOREIGN PATENT DOCUMENTS

| EP | 0126624 A2 | 11/1984 |
|---|---|---|
| EP | 0957811 B1 | 10/2004 |

(Continued)

*Primary Examiner* — Sean M Michalski
*Assistant Examiner* — Mirayda A Aponte
(74) *Attorney, Agent, or Firm* — Janeway Patent Law, PLLC; John M. Janeway (57) ABSTRACT

An apparatus for replicating a tooth within a user's mouth includes a threaded insert receivable with a bore in a wearer's jaw, the threaded insert having a first connector associated therewith and a tooth implant having a second connector. The first and second connectors are frictionally engageable with each other to retain the tooth implant within the user's mouth.

13 Claims, 9 Drawing Sheets

(56) References Cited

U.S. PATENT DOCUMENTS

| | | | | |
|---|---|---|---|---|
| 5,312,253 | A | * | 5/1994 | Chalifoux ............ A61C 8/0018 433/173 |
| 5,417,570 | A | * | 5/1995 | Zuest ................... A61C 8/0048 433/172 |
| 5,468,150 | A | | 11/1995 | Brammann |
| 5,782,918 | A | * | 7/1998 | Klardie .................. A61C 8/005 433/172 |
| 5,954,505 | A | | 9/1999 | Ford |
| 2006/0014120 | A1 | * | 1/2006 | Sapian ................. A61C 8/0057 433/173 |
| 2008/0261177 | A1 | | 10/2008 | Ford et al. |
| 2012/0202173 | A1 | * | 8/2012 | Seo ...................... A61C 8/0048 433/220 |

FOREIGN PATENT DOCUMENTS

| | | |
|---|---|---|
| ES | 2365090 A1 | 9/2011 |
| WO | 2013125924 A1 | 8/2013 |

* cited by examiner

TOOTH IMPLANT

BACKGROUND OF THE INVENTION

1. Field of Invention

The present invention relates to tooth implants in general and in particular to a method and apparatus for

2. Description of Related Art

The present invention is directed to an endosseous (endosteal) dental implant and a method of implantation thereof. Most endosteal dental implants are generally made of a body of elongated shape installed in a recess formed in the jawbone and they have a means for anchoring the implant within the bone as well as a means for receiving a prosthetic tooth. Generally, endosteal dental implants are placed by drilling an implant hole into the bone and inserting the implant into the prepared cavity by tapping and/or screwing.

Many different types of endosteal dental implants are known in the prior art. In particular, commonly many dental implants are formed of an insert which is installed in the user's jaw and abutment which is screwed to the insert. A cap may then be installed over the abutment. Such caps are commonly permanently secured to the abutment by adhering the cap over the abutment including the abutment screw which is used to secure the abutment to the insert. Therefore, in order to remove the implant, the entire cap must be removed or a hole must be drilled through the cap to access the abutment screw. Both of these procedures will require a new cap to be prepared or the old one repaired, which may difficult to provide an identical biting surface to the original cap. Disadvantageously, such bores must then thereafter be filled with a temporary or permanent filling material. The use of such a filling material within the bore is that that filling material must first be removed in order to extract the implant for future assessment or work on the patient and the filling material adds additional time and debris to the procedure. As such, the aim of the present invention is to provide and implant that makes it possible to address the cited drawbacks of known types of endosteal dental implants.

SUMMARY OF THE INVENTION

According to a first embodiment of the present invention there is disclosed an apparatus for replicating a tooth within a user's mouth comprising a threaded insert receivable with a bore in a wearer's jaw, the threaded insert having a first connector associated therewith and a tooth implant having a second connector. The first and second connectors are frictionally engageable with each other to retain the tooth implant within the user's mouth.

One of the first or second connectors may be rotationally fixed relative to each other. One of the first or second connectors may comprise a central cavity. The other of the first or second connectors may comprise a retaining post slidably receivable within the central cavity wherein the retaining post has an outline corresponding to the central cavity.

The central cavity may comprise a blind bore. The blind bore may include a keyed portion. The keyed portion may include a non-cylindrical shape. The keyed portion may comprise a groove extending longitudinally along the retaining post. The blind bore may include a retaining portion.

The retaining portion may comprise a tubular bore having at least one widened region. The retaining portion may include a plurality of biased fingers extending into the central cavity at a location corresponding to a groove around the retaining post. The central cavity may be located within an insert sleeve receivable within the threaded insert.

The apparatus may further comprise a washer between the insert and the tooth implant. The washer may be compressible. The apparatus may further comprise a flexible sleeve between the post and the cavity.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In drawings which illustrate embodiments of the invention wherein similar characters of reference denote corresponding parts in each view.

DETAILED DESCRIPTION

Figure 1:
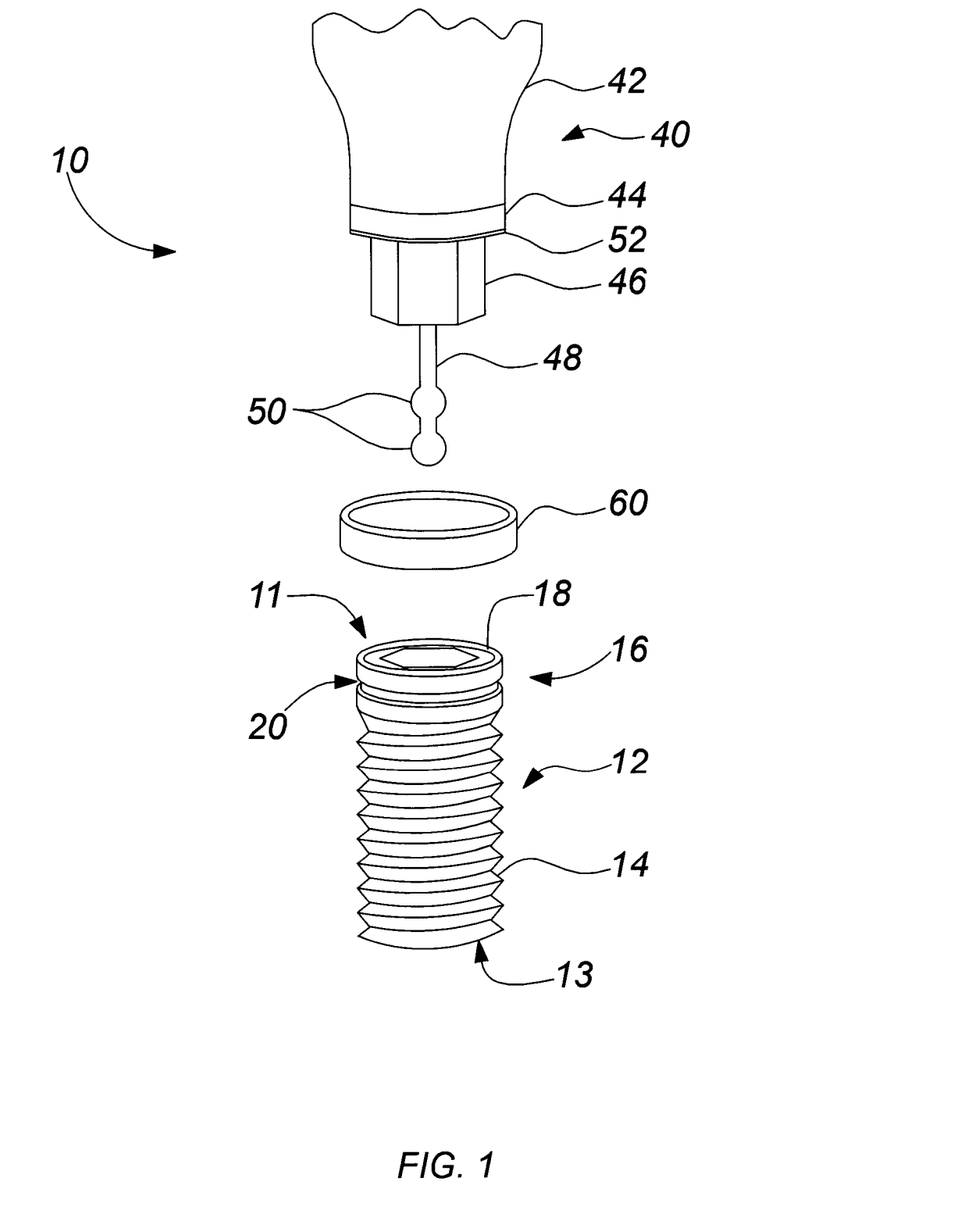
FIG. 1 is an exploded view of a tooth implant according to a first embodiment of the present invention.

Referring to FIG. 1, an apparatus for replacing a tooth according to a first embodiment of the invention is shown generally at 10. Turning to FIG. 1, the apparatus 10 comprises an threaded insert 12 adapted to be installed within the jaw of a patient and a tooth insert 40 which is slidably received within the threaded insert 12.

The threaded insert 12 comprises a substantially cylindrical member extending between top and bottom ends, 11 and 13, respectively with a threaded exterior 14 proximate to the bottom end 13 and a top shoulder portion 16 proximate to the top end 11. The shoulder portion 16 includes a top platform 18 and an annular groove 20 therearound as will be more fully described below. The threaded insert 12 is preferably made from zirconia, but may be made from any other suitable dental implant material as are commonly known. The threaded insert 12 is inserted into a bore in a patient's jaw (not shown) with the bottom end 13 first and thereafter screwed in such that the only visible part of the threaded insert 12 is the shoulder portion 16. The top platform 18 includes a bore 22 therethrough into the interior of the threaded insert 12 with a retaining lip 24 extending therefrom towards a center of the bore 22.

Figure 2:
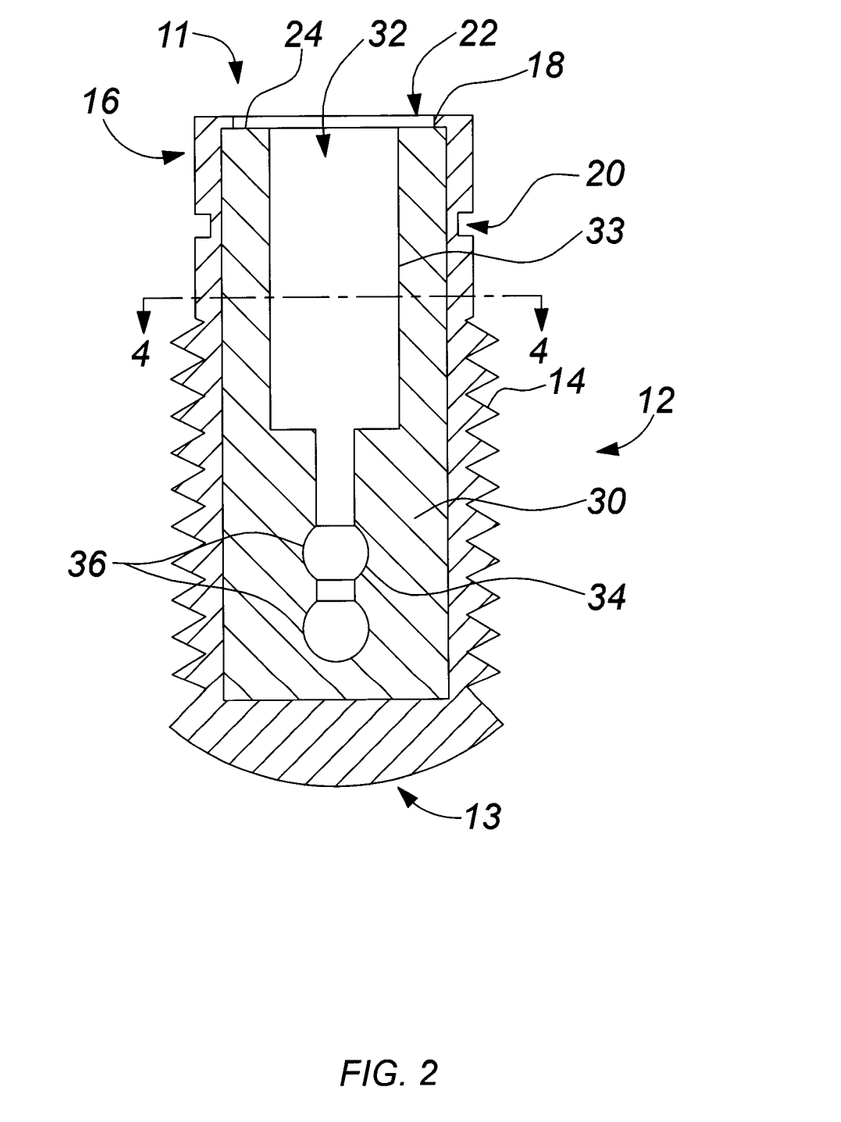
FIG. 2 is a cross-sectional view of the threaded insert of the implant of FIG. 1.

As shown in 2, the threaded insert 12 is lined with an insert sleeve 30 wherein the insert is held in place by the retaining lips 24. The insert sleeve 30 is formed of a substantially cylindrical member having outer dimensions corresponding to the dimensions of the bore 22. The insert includes a central cavity 32 therein having a top keyed portion 33 and bottom retaining portion 34. The top keyed portion 33 prevents the tooth insert 40 from rotating relative thereto while the retaining portion retains the tooth insert within the cavity as will be more fully described below. The insert sleeve 30 is formed of any suitable material, such as, by way of non-limiting example, Teflon and is slidably received within the bore 22. The insert sleeve 30 and/or bore 22 may also include longitudinal ridges (not shown) to prevent relative rotation between the two.

Figure 4A:
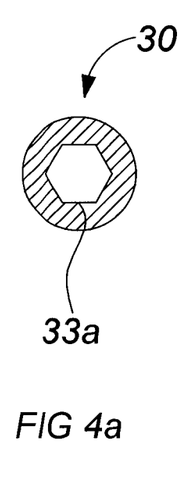
FIG. 4a is a top view of the alternative embodiments of the insert cavity opening.
Figure 4B:
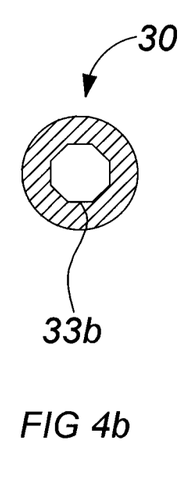
FIG. 4b is a top view of the alternative embodiments of the insert cavity opening.
Figure 4C:
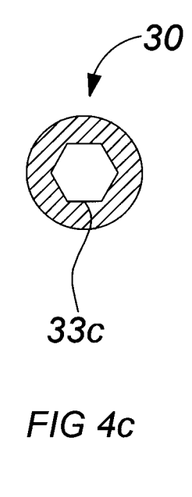
FIG. 4c is a top view of the alternative embodiments of the insert cavity opening.
Figure 4D:
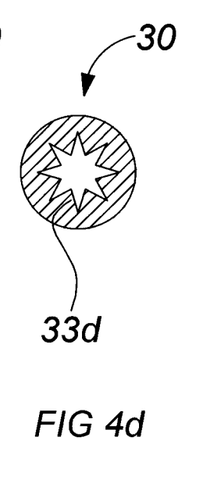
FIG. 4d is a top view of the alternative embodiments of the insert cavity opening.
Figure 6:
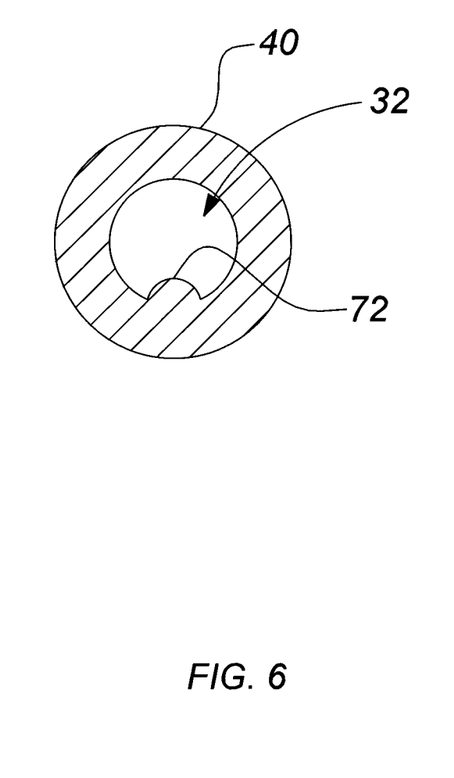
FIG. 6 is a bottom view of an opening in the tooth insert of FIG. 5.

The keyed portion 33 of the cavity 32 has a non-circular shape so as to provide surface which will engage the tooth insert and prevent rotation therebetween. As illustrated in FIGS. 4a through 4d, cross-section of the keyed portion may be selected to be any suitable shape, such as, by way of non-limiting example, octagonal 33b as illustrated in FIG. 4b, hexagonal 33a and 33c as illustrated in FIGS. 4a and 4c, torx 33d as illustrated in FIG. 4d or any other suitable non-circular shape, such as, by way of non-limiting example, oval, triangular, rectangular, irregular or the like. Optionally, the keyed portion 33 of the cavity may also include a ridge 72 extending therealong as illustrated in FIG. 6 adapted to fit a corresponding slot in the retaining post.

The retaining portion 34 comprises a narrowed portion of the cavity having a substantially cylindrical profile. Retaining portion 34 includes at least one widened region 36 located therealong. As illustrated, the retaining portion 34 may include two widened regions 36 although it will be appreciated that one or more than two may also be used. The widened regions 36 may be substantially spherical as illustrated although other cross-sectional profiles may be used as well.

With reference to FIG. 1, the tooth insert 40 comprises a top body 42 corresponding to the tooth which is to be replaced. The top body 42 may be formed of any suitable means as are commonly known in the art for creating replicas of missing or extracted teeth. The tooth insert 40 also includes a platform 44 which is secured to the bottom of the top body 42. The platform 44 is formed of any suitable material, such as, by way of non-limiting example, zirconia. Extending from a lower edge of the platform 44 is a key 46 having an outline corresponding to the keyed portion 33 of the insert sleeve 30. Furthermore, a retaining post 48 extends below the keyed portion 33 in a position and size corresponding to the retaining portion 34 of the insert. In particular, the retaining post 48 has an outer cylindrical shape corresponding to the retaining portion 34 with widened flanges 50 located therealong as positions corresponding to the widened regions 36 of the insert sleeve 30. The width of the widened flanges 50 is selected to be greater than the diameter of the main portions of the retaining portions 34 so as to retain the widened flanges 50 within the widened regions 36 and thereby prevent unwanted removal of the tooth implant as will be more fully described below. As illustrated, the tooth insert 40 may also include an o-ring 52 or other suitable seal around the bottom outside edge of the platform 44. Optionally, the platform 44 may include a silicon sleeve 60 adapted to be received therearound as will be more fully described below.

Figure 3:
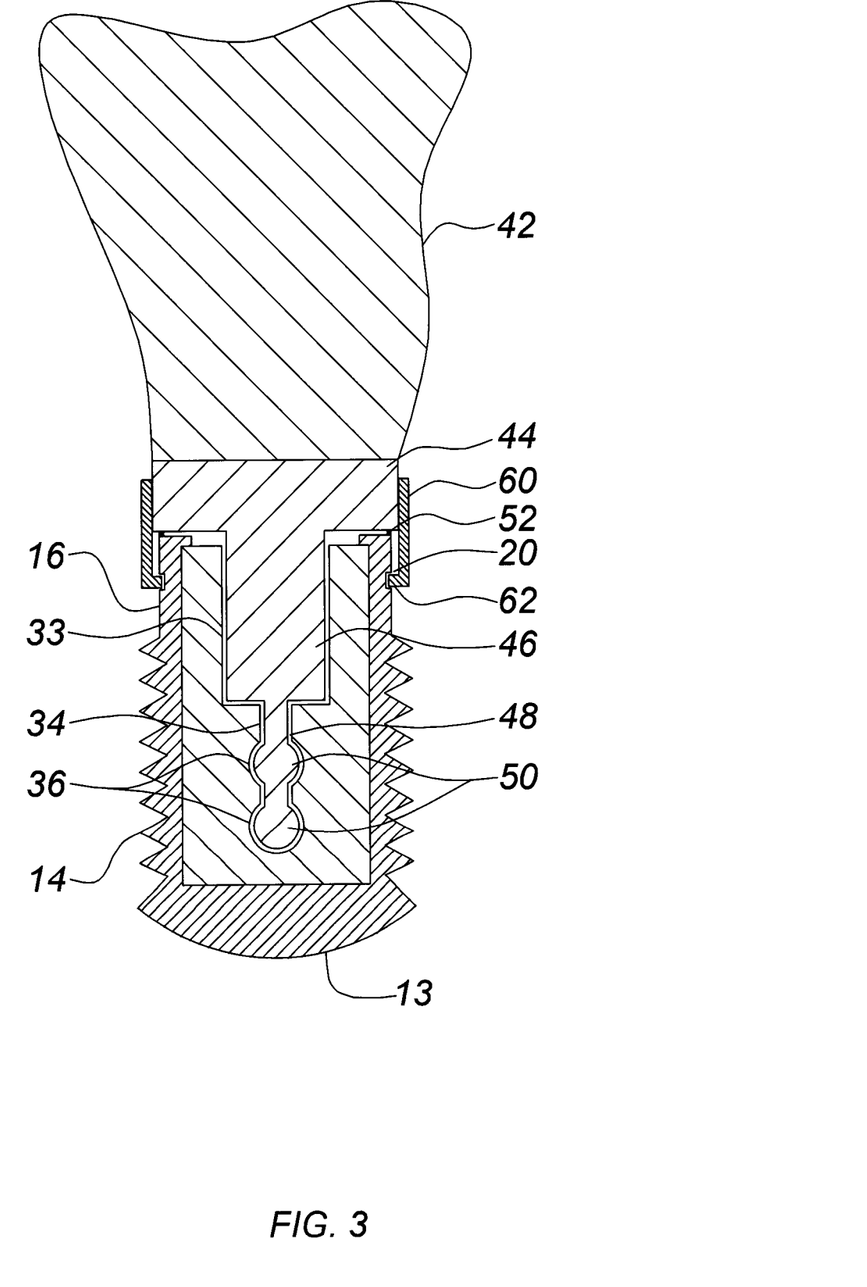
FIG. 3 is across-sectional view of the tooth insert and threaded insert as assembled together.

In operation, the threaded insert 12 is threadably installed within a bore in a patient's jaw according to known methods. Thereafter, the insert sleeve 30 is installed within the bore 22 thereof. The orientation of the keyed portion 33 of the cavity may then be checked utilizing methods known in the prior art, such as the use of an indicator cap. From the orientation of the keyed portion 33 and the tooth to be replaced, the tooth insert 40 may be prepared to correspond to the tooth to be replaced and with the keyed portion 46 and retaining post 48 positioned relative to the top body 42 to position the tooth as desired. Once prepared, the silicon sleeve 60 may be installed around the platform 44 and rolled up to expose the bottom edge thereof. The tooth insert 40 may then be inserted into the cavity 32 by aligning the keyed portion 46 of the tooth insert 40 with the keyed portion 33 of the cavity 32. The retaining post 48 is then pressed into the retaining portion 34 of the cavity such that the material of the insert sleeve 30 is deformed to permit the widened flanges 50 to be positioned into the widened regions 36 of the cavity. Such a position is illustrated in FIG. 3 wherein the o-ring 52 is positioned between the platform 44 of the tooth insert 40 and the top platform 18 of the threaded insert 12. Thereafter the sleeve 60 may be rolled down to cover the gap between the tooth insert and the threaded insert 12 such that a bottom ridge 62 on the silicon sleeve is engaged within the annular groove 20.

Figure 5:
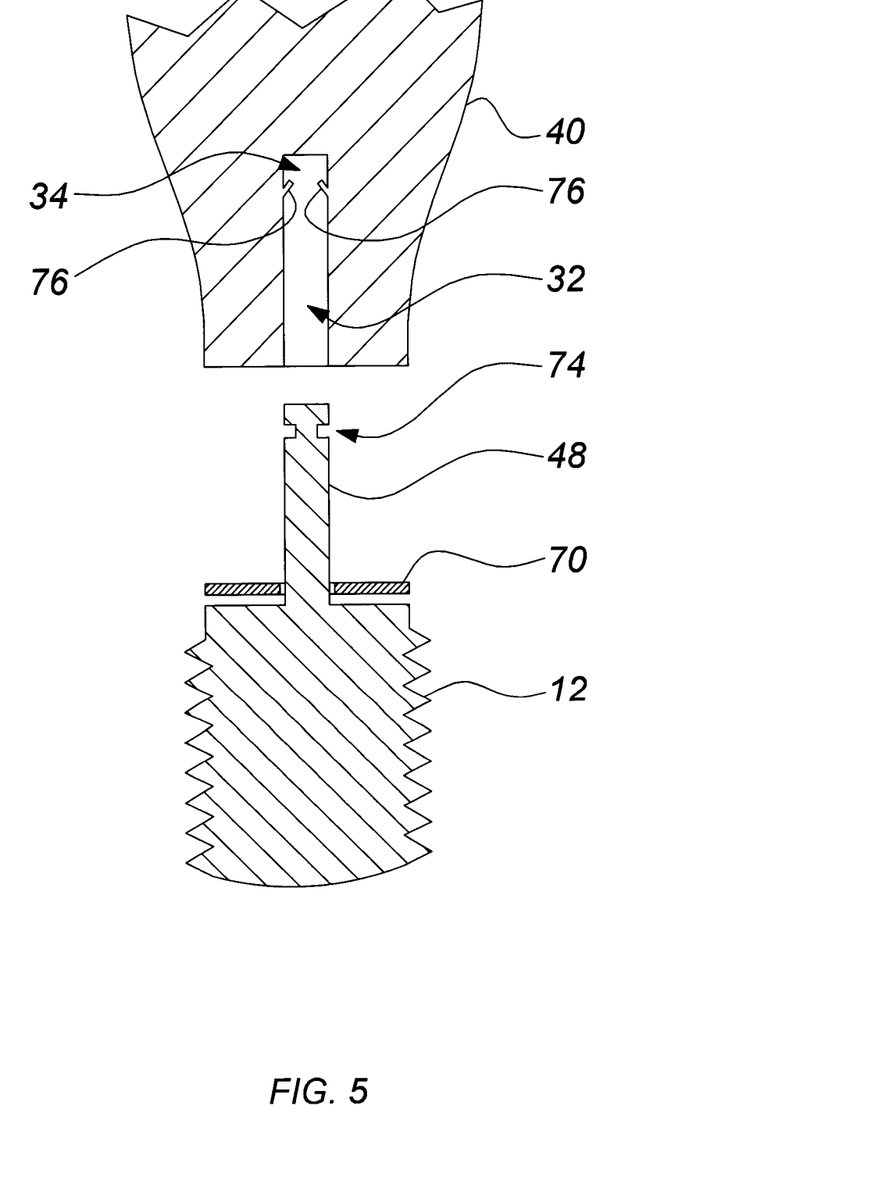
FIG. 5 is a cross-sectional view of a tooth implant according to a first embodiment of the present invention.

Optionally as illustrated in FIG. 5, the tooth insert 40 may include the central cavity 32 wherein the retaining post 48 extends from the threaded insert 12. As illustrated in FIG. 5, the retaining post 48 may include an annular groove 74 therearound wherein the central cavity 32 includes a plurality of inwardly biased fingers 76 extending therefrom at a position adapted to engage within the groove 74 and retain the tooth insert thereon. As illustrated in FIG. 5, the apparatus may optionally include a silicone washer 70 or other suitable compression cushioning device between the threaded insert 12 and the tooth insert 40.

Figure 7:
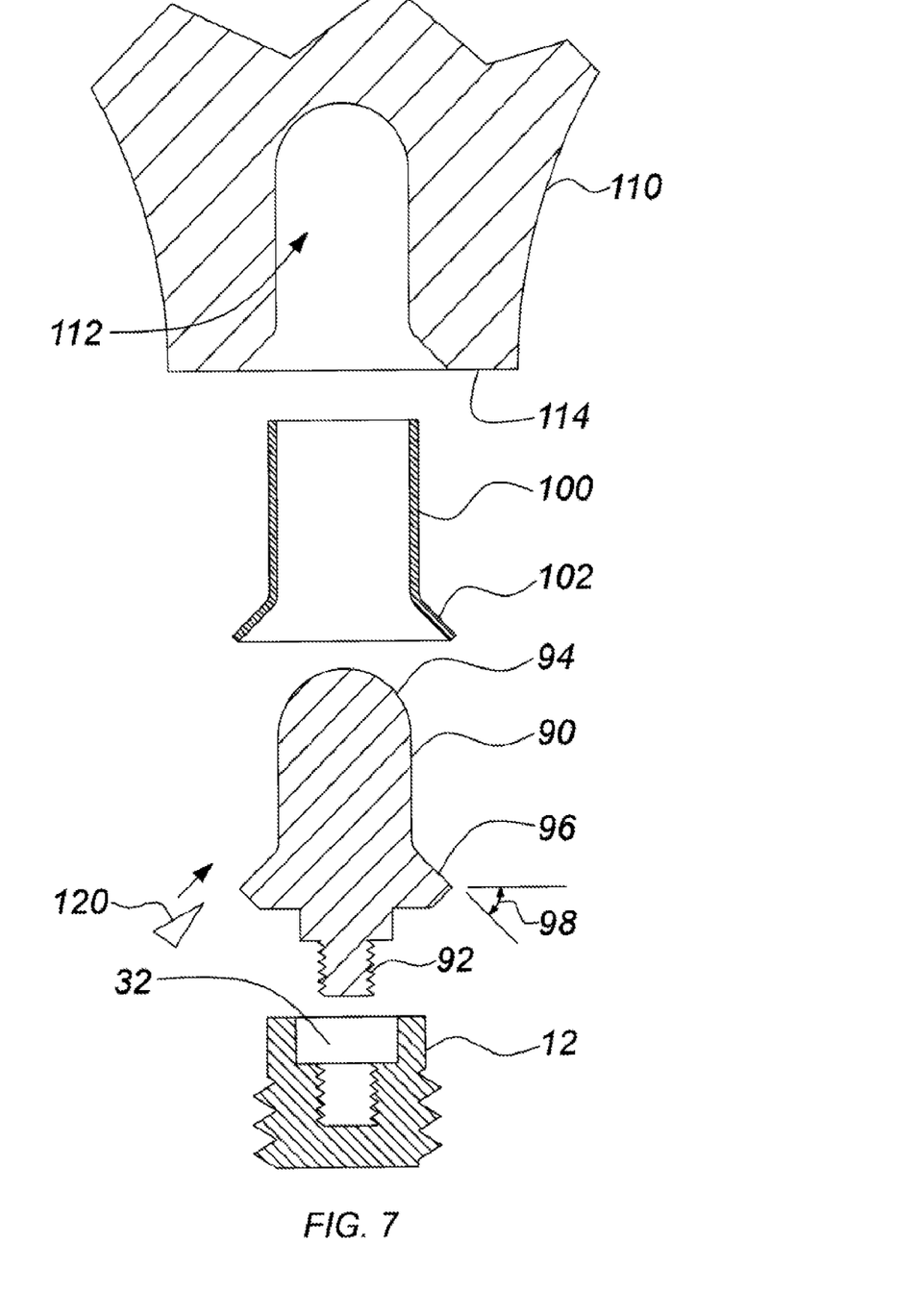
FIG. 7 is an exploded view of a tooth implant according to a first embodiment of the present invention.
Figure 8:
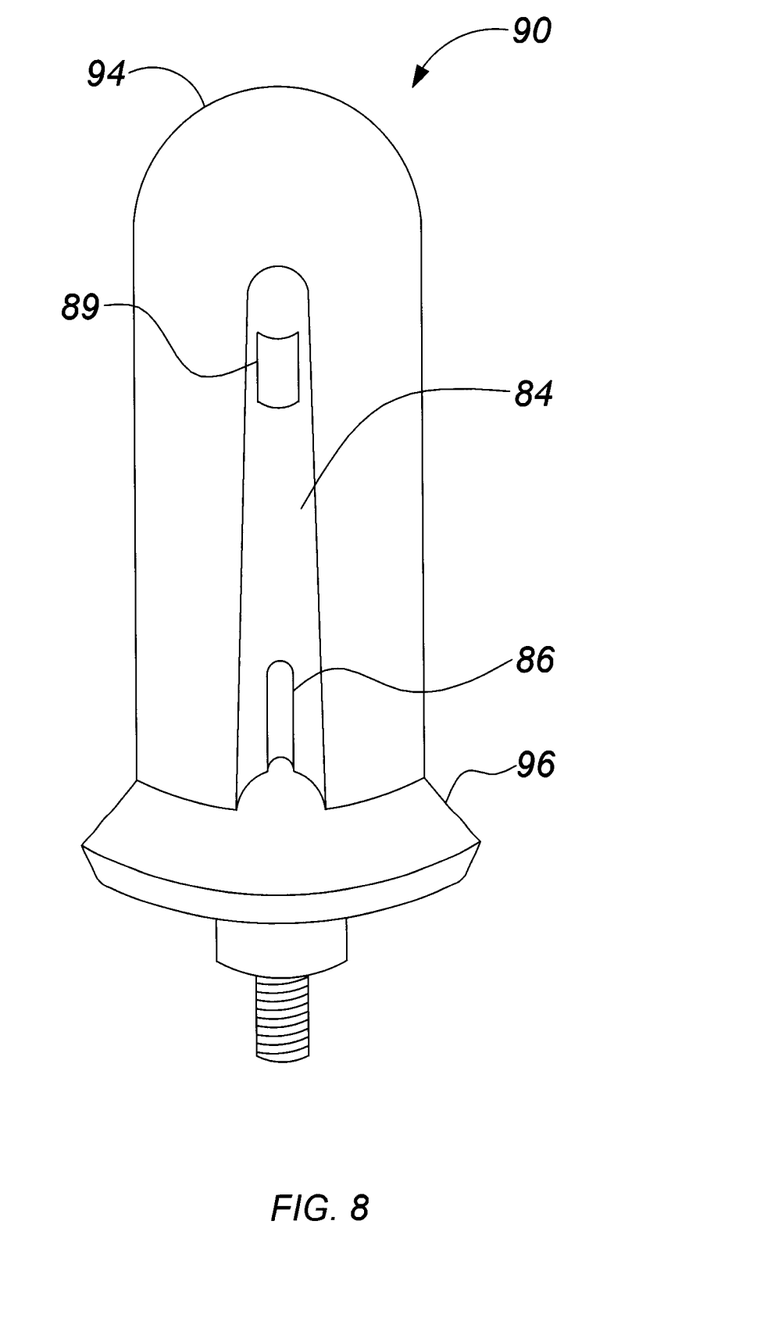
FIG. 8 is detailed perspective view of the retaining post of FIG. 7
Figure 9:
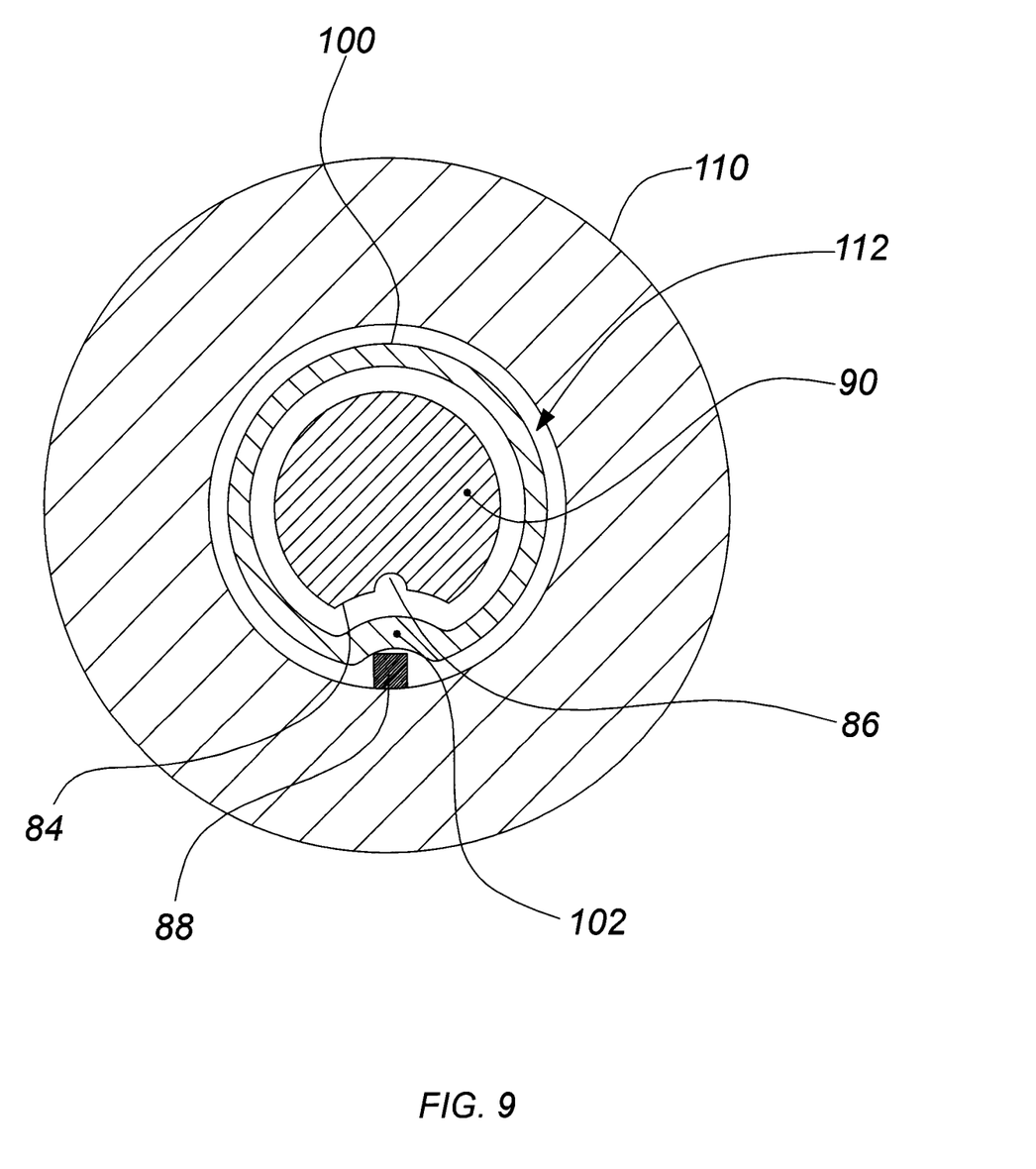
FIG. 9 is a cross sectional view of the tooth implant of FIG. 7

Turning now to FIGS. 7 through 9, an optional embodiment of the present invention is illustrated in which as separate retaining post 90 is provided as a separate element which may be secured to the threaded insert 12. In particular, the threaded insert 12 may include a threaded central cavity 32 extending thereinto corresponding to a threaded post 92 extending from the bottom of the retaining post 90. The assembly of FIGS. 7 through 9 also includes a tooth insert 110 with a cavity 112 thereinto sized to be received upon the retaining post 90 with a gasket sleeve 100 therebetween.

As illustrated in FIG. 8, the retaining post 90 may include a rounded top end 94 and an outwardly flared bottom end 96. As illustrated in FIG. 7, the bottom may have an outwardly outer surface which is oriented at an angle generally indicated at 98 of between 20 and 45 degrees below horizontal, the purpose of which will be more fully described below. The retaining post 90 may have a substantially circular cross section with one or more optional groove 84 extending longitudinally along one side thereof for providing resistance to rotation of the tooth insert 40. The groove 84 may optionally include secondary groove 86 therein proximate to a bottom end thereof, the purpose of which will be more fully described below. An optional identification of the retaining post 89 may also be included thereon, such as by way of non-limiting example, a serial number, bar code or the like.

The gasket sleeve 100 may be formed of any suitable material, such as Teflon® or the like so as to be flexible. The thickness of the gasket sleeve 100 is selected to be greater than the difference between the radius of the cavity 32 and the retaining post 90 so as to cause an interference fit therebetween, such as approximately 0.0004 inches (10 microns). As illustrated in FIG. 9, the gasket sleeve 100 may optionally include a thicker portion 102 corresponding to the groove 84 extending along the retaining post.

In operation, after the threaded insert 12 is located within the jaw of the patient according to known methods, the retaining post 90 is threadably secured onto the threaded insert 12 by threadably connecting the threaded post 92 onto the threaded cavity 32. Thereafter, the tooth insert 110 may be test fitted onto the retaining post 90 for alignment and height. The height of the tooth insert 110 may be adjusted by removing material from the bottom 114 of the tooth insert. Once the alignment and height of the tooth insert 110 is correct the gasket sleeve 100 may be inserted into the cavity 112 and retained therein by a light cement after which the alignment of the tooth insert 110 within the mouth of the patient may again be checked and adjusted. By removing material from the bottom 114 of the tooth insert or adjusting the orientation of the gasket sleeve 100 within the cavity 112. Once the orientation and height of the tooth insert 110 is acceptable, a key 88 is then positioned under the gasket sleeve at a position corresponding to the secondary groove 86 and the tooth insert 110 pressed over the retaining post 90 until the key 88 is positioned within the secondary groove 86 so as to extrude the gasket sleeve 100 into the groove 84 and secondary groove 86 thereby retaining the tooth insert 110 on the retaining post 90. When a tooth insert 110 is desired to be removed, one or more wedges 120 may be forced between the bottom 114 of the tooth insert 110 and the flared bottom end 96 of the retaining post 90 so as to separate the two after which the tooth insert may be pulled off the retaining post.

While specific embodiments of the invention have been described and illustrated, such embodiments should be considered illustrative of the invention only and not as limiting the invention as construed in accordance with the accompanying claims.

What is claimed is:

1. An apparatus for replicating a tooth within a user's mouth, the apparatus comprising:
    a threaded insert receivable with a bore in a wearer's jaw, the threaded insert having a first connector;
    a tooth insert having a second connector in a bottom surface thereof and a top body corresponding to the tooth which is to be replaced;
    wherein one of said first and second connectors comprises a post and wherein said other of said first and second connectors comprises a socket adapted to receive said post;
    a flexible sleeve sized to surround and extend the length of said post so as to be located radially between said first and second connectors along a length of said post;
    wherein said first and second connectors are frictionally engageable with each other;
    a groove in the post extending longitudinally along an outer surface of said post, said groove having a secondary groove therein that is smaller than the groove and also in the post; and
    a key separate from the post and the sleeve, and sized to be retained within said secondary groove with the flexible sleeve between the key and the secondary groove to retain said post upon said socket thereby retaining said tooth insert within said user's mouth.

2. The apparatus of claim 1 wherein said first and second connectors are rotationally fixed relative to each other.

3. The apparatus of claim 1 wherein:
    the first connector comprises a central cavity and the post is releasably held in the central cavity, and
    the socket receives the post to retain the tooth insert with the threaded insert.

4. The apparatus of claim 3 wherein the post is slidably receivable within said socket of the second connector, and said post has an outline corresponding to said socket.

5. The apparatus of claim 3 wherein said central cavity comprises a blind bore.

6. The apparatus of claim 5 wherein said blind bore includes a keyed portion.

7. The apparatus of claim 6 wherein said keyed portion includes a non-cylindrical shape.

8. The apparatus of claim 3 wherein said central cavity includes a retaining portion.

9. The apparatus of claim 8 wherein said retaining portion comprises a tubular bore having at least one widened region.

10. The apparatus of claim 3 wherein said central cavity is located within an insert sleeve receivable within the threaded insert.

11. The apparatus of claim 3 wherein the first connector's central cavity includes threads for threadingly engaging a threaded portion of the post to releasably attach the post to the central cavity.

12. The apparatus of claim 1 wherein the key includes a cross-section that is square.

13. The apparatus of claim 1 wherein said socket includes a retaining portion.

* * * * *